United States Patent [19]

Dale

[11] 4,232,659
[45] Nov. 11, 1980

[54] VEIN HOLDER ASSEMBLY

[75] Inventor: William A. Dale, Nashville, Tenn.

[73] Assignee: Codman and Shurtleff, Inc., Randolph, Mass.

[21] Appl. No.: 1,799

[22] Filed: Jan. 8, 1979

[51] Int. Cl.³ .............................................. A61B 19/00
[52] U.S. Cl. .................................... 128/1 R; 73/49.1; 248/49; 248/201
[58] Field of Search ...................... 128/1 R; 73/38, 40, 73/49.1, 49.5; 248/49, 70, 75, 201; 211/175

[56] References Cited

U.S. PATENT DOCUMENTS

| 2,051,712 | 8/1936 | Holt | 248/201 |
|---|---|---|---|
| 2,561,540 | 7/1951 | Sherbrooke | 248/49 |
| 3,916,874 | 11/1975 | Perrin | 128/1 R |

FOREIGN PATENT DOCUMENTS 2713093  9/1978  Fed. Rep. of Germany ...... 128/334 R

Primary Examiner—Dalton L. Truluck
Attorney, Agent, or Firm—Donal B. Tobin

[57] ABSTRACT

A vein holder assembly for use in the preparation of a vein segment during surgery comprises a base and a first vein support connected to the base and adapted to close off one end of the vein segment. A second vein support is connected to the base spaced from the first vein support. This second vein support is adapted to allow fluid to pass into the vein segment while the same is being supported. To accommodate different length vein segments, the spacing between the first and second vein supports is adjustable.

4 Claims, 4 Drawing Figures

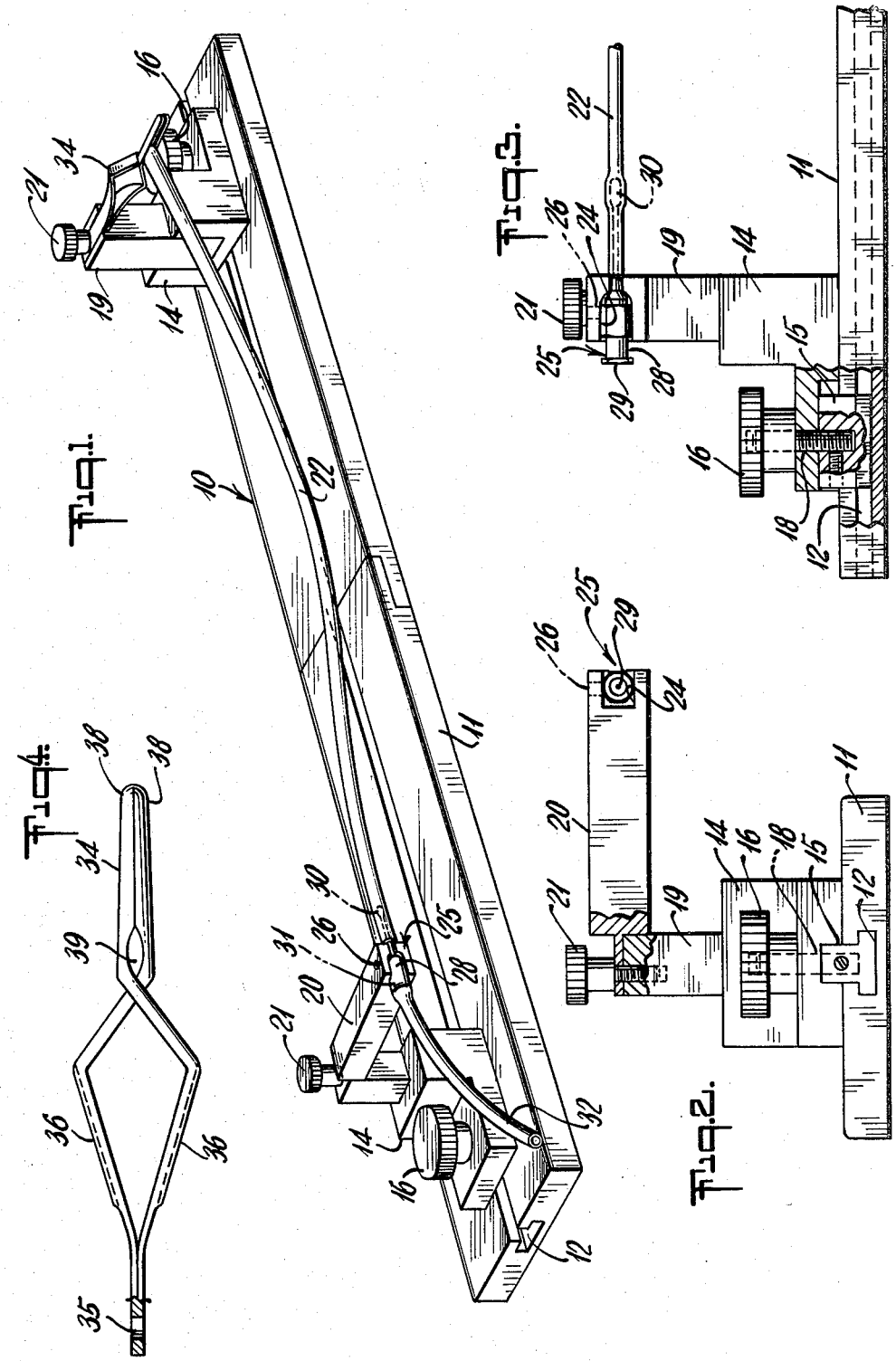

VEIN HOLDER ASSEMBLY

BACKGROUND OF THE INVENTION

The present invention relates to a device for supporting a vein segment in the preparation of the same during surgery.

In the event of an arterial blockage, impediment, damage or the like, it is known to graft a vein or vein segment from one part of the body and implant the graft in the area where the blockage has occurred in order to effectively bypass the problem area. For instance, the great saphenous vein may be taken from the leg and used for a coronary artery bypass or for a femoral popliteal artery bypass or other similar operations. In this procedure, the vein is removed from the leg and may be mounted on a holder so that it may be prepared for implantation in its new location in the body. Most procedures of this type have required two persons to perform the operation of extracting the vein to be prepared, the actual preparation of the vein and then its re-implantation. This, of course, undesirably adds expense and takes the time and effort of an additional person when one person should be in a position to complete the job.

A device for use in the preparation of a severed length of vein for grafting purposes is disclosed in U.S. Pat. No. 3,916,874. In that patent, the device includes a frame having a base and two spaced, upstanding brackets which receive an elongated core thereon. This core is used for distending the vein with liquid in order to simulate normal blood pressure. While this type vein holder device may allow the vein preparation operation to be handled by one person, there are still some shortcomings. For instance, the surgeon is required to seal the vein ends by encircling the same with tape and weighting the tape with a clamp on each end. In addition, the frame device is intended to hold a core of one particular size which may prove inconvenient for handling vein lengths of varying dimensions that may be necessary depending upon the graft being contemplated. Accordingly, it can be seen that there is room for further improvements in this field.

SUMMARY OF THE INVENTION

A vein segment holder comprises a base and first vein supporting means connected to the base and adapted to close off one end of the vein segment. A second vein supporting means is connected to the base and is spaced from the first vein supporting means. This second veing supporting means is adapted to allow fluid to pass into the vein segment while the same is being supported. To accommodate different length vein segments, the spacing between the first and second supporting means is adjustable.

In the preferred embodiment of the present invention, the base is elongate in construction and has a groove in its elongate direction. Both the first and second vein supporting means are mounted on respective slide means which are adapted to slide in the groove in the base. Adjustable tightening knobs are associated with each slide means for tightening the same in a selected position on the base. This, of course, provides for the adjustability of the spacing between the two vein supporting means and thus accommodates vein segments of different lengths. Preferably, one of the vein supporting means is a clamp which is used to close off one end of the vein segment while being supported. The other vein supporting means preferably includes a connector with a hollow tube extending therefrom. The tube is adapted to be inserted into the end of a vein segment to provide internal support therefor; the connector is adapted to receive a mating connector so that fluid can be delivered therethrough and through the hollow tube and thereby into the vein segment while the vein segment is closed off at its other end. Thus, the vein segment may be maintained in a fluid distended condition while it is being prepared for implantation.

From the structural standpoint, the vein holder assembly of the present invention is notably different from prior vein holding devices in a number of respects. For instance, the present vein holder assembly includes vein clamping means connected to the base for closing off one end of the vein segment. Also connected to the base, preferably at the other end thereof, is the vein supporting means for, not only supporting the other end of the vein segment, but also for allowing fluid to pass into the vein segment in order to keep the same distended. Another structural difference is the adjustability of the spacing between the vein supporting means so that different lengths of vein segments may be prepared conveniently.

Thus, one of the advantages of the present invention is its functional convenience which permits one person to handle the vein grafting operation and preparation. Another advantage lies in the vein supporting means wherein the ends of the vein segment are tied and closed while mounted on this holder assembly without the need for weighting clamps as taught by the prior art. A further advantage is the adjustability of the spacing between the vein supporting means to handle various size vein segments for different operations and purposes.

BRIEF DESCRIPTION OF THE DRAWINGS

FIG. 1 is a perspective view illustrating the preferred vein holder assembly of the present invention with a vein segment exemplified in position during its preparation for implantation;

FIG. 2 is an end view of the preferred vein holder assembly illustrating the end with the vein supporting means thereon;

FIG. 3 is a partial elevational view of the preferred vein holder assembly illustrating the connection of the vein supporting means to the base; and FIG. 4 is the preferred embodiment of the vein clamp.

DETAILED DESCRIPTION

While this invention is satisfied by embodiments in many different forms there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be pointed out in the appended claims.

Adverting to the drawings there is illustrated a vein holder assembly 10 for use in the preparation of a vein segment during surgery. Vein holder assembly 10 includes an elongate, generally flat base 11. The elongate nature of base 11 provides more flexibility to the assembly inasmuch as vein segments of greater length may be handled thereon. A groove 12 is included in base 11 and extends along the elongate direction of the base and is substantially along its center line. Groove 12 is preferably a "T-slot" channel which may be conveniently formed in the base by a number of different techniques, including standard machine-shop operations. The surfaces of groove 12 are preferably made as smooth as possible since the groove is intended to act as a guide for sliding the components which support the vein segment.

A slide block 14 is positioned on the top surface of base 11 and is connected thereto by means of a "T-guide" 15, as more clearly illustrated in FIGS. 2 and 3. T-guide 15 mates with and is adapted to slide in groove 12 so that the stem of the T-guide projects upwardly into slide block 14. A knob 16 is provided on block 14, and is adapted to receive a threaded pin or a screw 18. Screw 18 is also threaded into the stem of T-guide 15, so that turning knob 16 in one direction will tighten slide block 14 in a fixed position on base 11. Turning knob 16 in the opposite direction will loosen the connection thereby allowing slide block 14 to slide along base 11 if an adjustment in the spacing for holding a specific length vein segment is required. The operator of this assembly thus has a convenient means for locking the slide block in position, and then unlocking the same to provide for changes in the spacing.

A vertical arm 19 projects upwardly from slide block 14 in order to provide additional height as a convenience for the user. Of course, arm 19 may be omitted, if desired. A horizontal arm 20 is attached to vertical arm 19 by means of thumb knob 21. Horizontal arm 20 serves as a supporting member for holding one end of a vein segment 22 for its preparation for implantation in the body. Knob 21 is adjustable to allow arm 20 to extend to either side of the slide block, or to make minor adjustments, if necessary. At the distal end of arm 20, a notch 24 is provided. This notch is adapted to receive vein support 25, as more clearly illustrated in FIGS. 2 and 3. A set screw 26 is provided to hold vein support 25 in place.

Vein support 25 includes a connector 28 having a passage 29 therethrough. A hollow tube 30 extends from connector 28 with its hollow portion communicating with passage 29 so that fluid may pass through connector 28 and hollow tube 30. During preparation of vein segment 22 for surgical purposes, the end of the vein segment is slid over tube 30 onto connector 28, and the connector and the end of the vein segment is tightened in position in notch 24. Connector 28 is adapted to receive a mating connector 31 as more clearly illustrated in FIG. 1. Mating connector 31 allows fluid, delivered through tube 31, to pass through connector 28 and hollow tube 30 and then into vein segment 22. This fluid maintains vein segment in a distended condition so that it may be prepared for its intended purpose. It is noted that hollow tube 30, in addition to providing fluid delivery to the vein segment, also provides support to that end of the vein segment.

A second slide block 14 is also slidably connected to base 11 and includes the same type provisions, including adjustable knob 16, for allowing it to slide along the base and be tightened and locked into position. Thus, with the spacing between slide blocks being adjustable, this vein assembly readily accommodates different length vein segments. Extending substantially horizontally from vertical arm 19 of the second slide block is a vein clamp 34. Vein clamp 34 is maintained in position on its vertical arm 19 by means of an adjustable thumb knob 21 similar in most respects to the thumb knob on the first slide block. Thus, vein clamp 34 may be adjusted to extend to either side of the assembly depending upon the orientation of the assembly during use. As seen more clearly in FIG. 4 in conjunction with FIG. 1, vein clamp 34 is preferably a spring-type clamp which is spring-biased to remain closed under static conditions. A through-hole 35 is included in the flat end of the clamp so that adjustment knob 21 may tighten the clamp to the block assembly. Spring arms 36 of clamp 34 are squeezed toward each other by the user thereby opening jaws 38. The other end of vein segment 22 is then inserted in the small indentation 39 between jaws 38. The jaws are allowed to close and vein segment 22 is then squeezed between jaws 38 to effectively close off that end of the vein segment. With this end of vein segment 22 closed off, fluid entering the vein segment at its other end will fill the vein segment and thus maintain it in a distended condition. This, of course, simulates normal blood pressure upon which the vein is accustomed. Vein clamp 34 thus closes off one end of the vein segment and supports that end during the preparation of the vein for its subsequent implantation in the body. It is appreciated that vein clamp 34 may be constructed of many different materials, but is preferably a metallic spring material.

The vein holder assembly of the present invention may conveniently be constructed from many different materials, but is preferably made to be readily disassembled and compatible with autoclaving procedures. Furthermore, the components of this vein holder assembly may optionally be colored in order to prevent undesirable flashes of light when it is being used in the operating room.

Thus, the present invention provides a vein holder assembly for use in the preparation of a vein segment during surgery and which allows this surgical operation to be handled by one person. Furthermore, the adjustability of the respective vein supporting components readily accommodates different length vein segments thereby providing the capability for multi-purpose uses.

What is claimed is:

1. A vein holder assembly for use in the preparation of a vein segment during surgery comprising: an elongate base having a groove in its elongate direction; first slide means connected to said base and adapted to slide in said groove; first adjustable tightening means associated with said first slide means for tightening the same in a selected position on said base; a vein clamp mounted on said first slide means for closing off one end of a vein segment; second slide means connected to said base and adapted to slide in said groove; second adjustable tightening means associated with said second sliding means for tightening the same in a selected position on said base; a vein support mounted on said second slide means adapted to allow fluid to pass into said vein segment while supporting the same and while the other end of said vein segment is closed off by said vein clamp whereby said vein segment may be maintained in a fluid distended condition.

2. A vein holder assembly as defined in claim 1 wherein said first and second tightening means each include an adjustable knob associated with each of said clamping and supporting means for locking each in position and for unlocking the same to change the spacing therebetween.

3. A vein holder assembly as defined in claim 1 wherein said vein clamping means is a spring clamp adapted to remain closed under static conditions.

4. A vein holder assembly as defined in claim 1 wherein said vein support includes a connector having a passage therethrough and a hollow tube extending from said connector, said hollow portion communicating with said passage, said tube adapted for insertion into one end of said vein segment to provide internal support therefor, said connector adapted to receive a mating connector so that fluid can be delivered therethrough and through said hollow tube and into said vein segment while said vein segment is closed off at its other end whereby said vein segment may be maintained in a fluid distended condition.

* * * * *